United States Patent [19]
Yoon

[11] Patent Number: 5,665,096
[45] Date of Patent: Sep. 9, 1997

[54] NEEDLE DRIVING APPARATUS AND METHODS OF SUTURING TISSUE

[76] Inventor: InBae Yoon, 2101 Highland Ridge Dr., Phoenix, Md. 21131

[21] Appl. No.: 399,984

[22] Filed: Mar. 7, 1995

[51] Int. Cl.⁶ .................................................. A61B 17/10
[52] U.S. Cl. .......................... 606/139; 606/144; 606/148; 606/223
[58] Field of Search ........................... 606/139, 144, 606/148, 151, 223, 224

[56] References Cited

U.S. PATENT DOCUMENTS

| | | |
|---|---|---|
| 671,337 | 4/1901 | Gibson . |
| 2,646,045 | 7/1953 | Priestley . |
| 3,139,089 | 6/1964 | Schwerin . |
| 3,168,097 | 2/1965 | Dormia . |
| 3,871,379 | 3/1975 | Clarke . |
| 3,946,740 | 3/1976 | Bassett . |
| 3,985,138 | 10/1976 | Jarvik . |
| 4,103,690 | 8/1978 | Harris . |
| 4,164,225 | 8/1979 | Johnson et al. . |
| 4,621,640 | 11/1986 | Mulhollan et al. . |
| 4,784,139 | 11/1988 | Demos . |
| 4,890,615 | 1/1990 | Caspari et al. . |
| 4,935,027 | 6/1990 | Yoon . |
| 5,015,250 | 5/1991 | Foster . |
| 5,037,433 | 8/1991 | Wilk et al. . |
| 5,100,418 | 3/1992 | Yoon ........................ 606/139 |
| 5,152,769 | 10/1992 | Baber . |
| 5,207,694 | 5/1993 | Broome ..................... 606/148 |
| 5,234,443 | 8/1993 | Phan et al. . |
| 5,281,236 | 1/1994 | Bagnato et al. . |
| 5,336,229 | 8/1994 | Noda . |
| 5,336,231 | 8/1994 | Adair . |
| 5,356,424 | 10/1994 | Buzerak et al. ............ 606/223 |
| 5,364,408 | 11/1994 | Gordon ..................... 606/144 |
| 5,366,459 | 11/1994 | Yoon ........................ 606/151 |
| 5,387,221 | 2/1995 | Bisgaard . |
| 5,391,174 | 2/1995 | Weston ...................... 606/148 |

*Primary Examiner*—Michael Buiz
*Assistant Examiner*—Mark S. Leonardo

[57] ABSTRACT

An apparatus for suturing anatomical tissue includes a hollow needle guide having a distal end, a needle disposed within the needle guide and movable between a retracted position where at least a portion of the needle is disposed within the needle guide and an extended position where the needle is disposed externally of the needle guide, suture material connected with the needle, and a manually articulable needle receiver for guiding a distal end of the needle as a proximal end of the needle is advanced distally through the needle guide and capturing the needle when the proximal end of the needle emerges from the distal end of the needle guide.

40 Claims, 8 Drawing Sheets

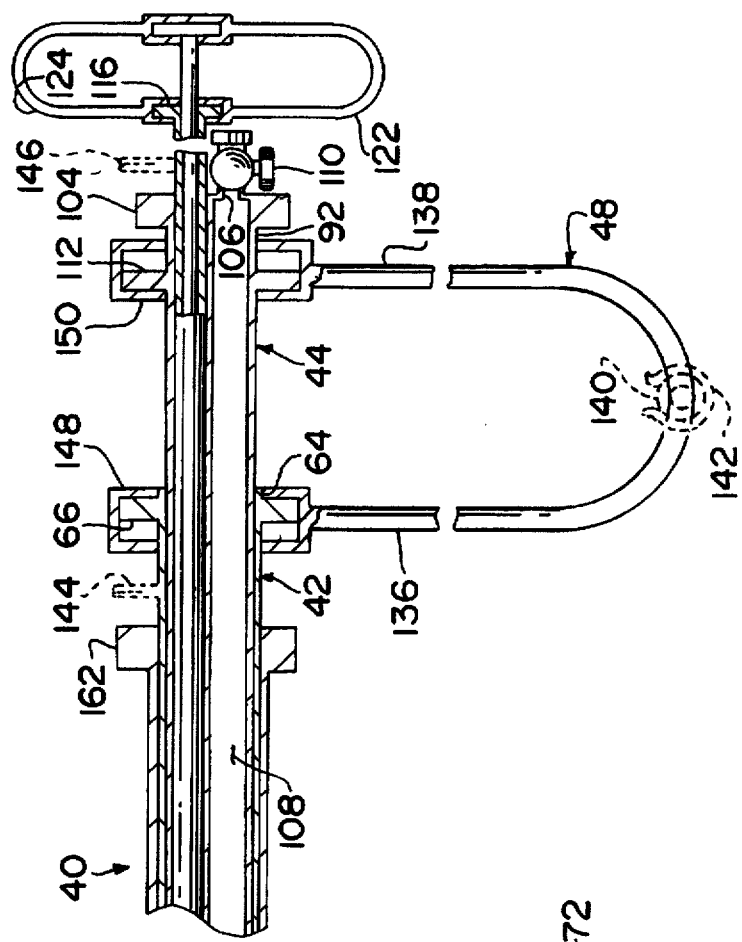
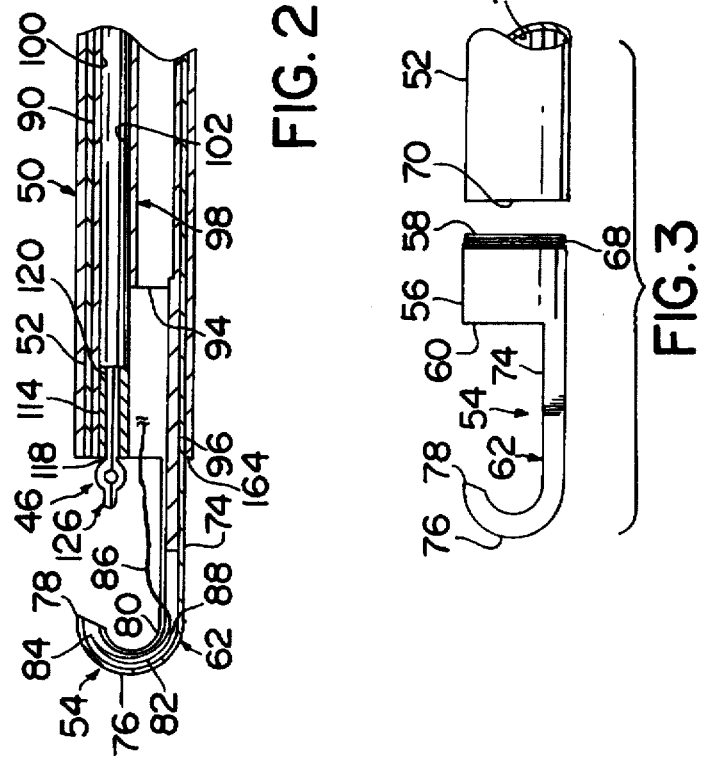
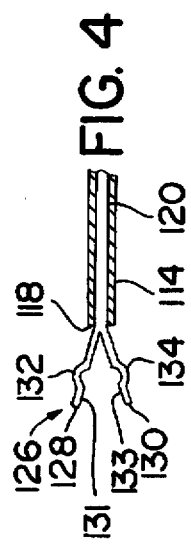
FIG. 2
FIG. 3
FIG. 4

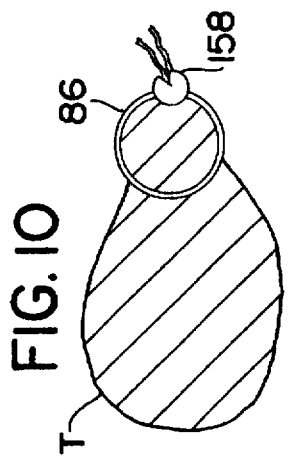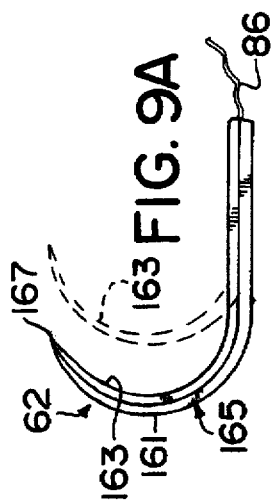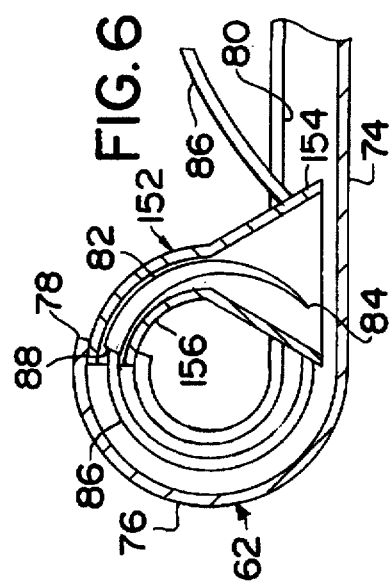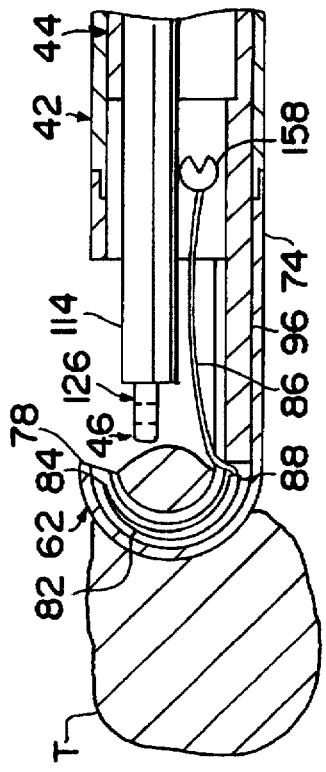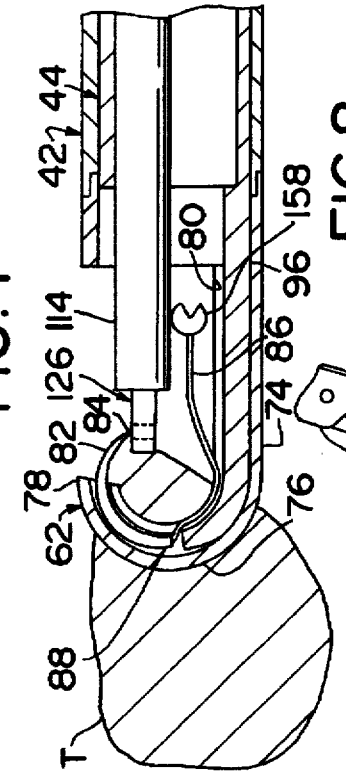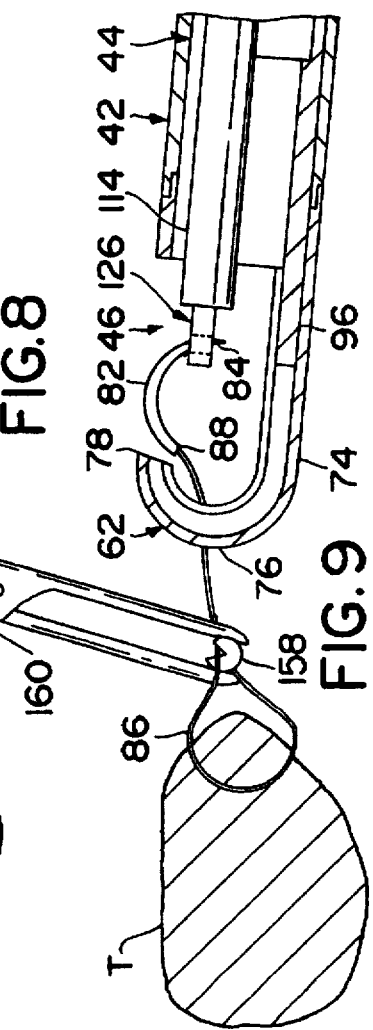

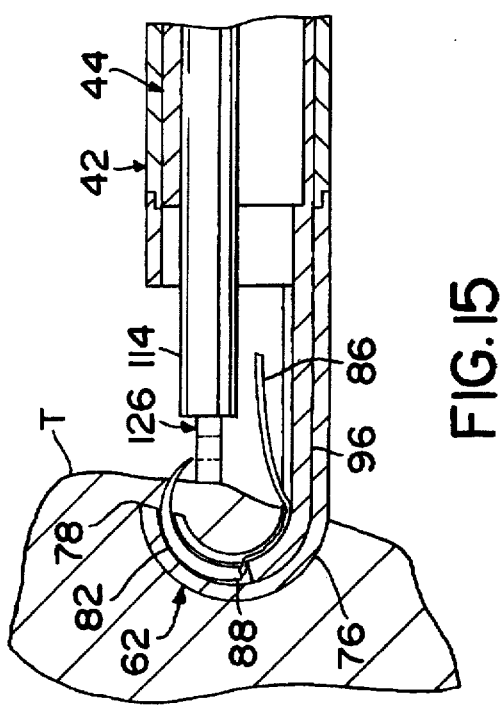
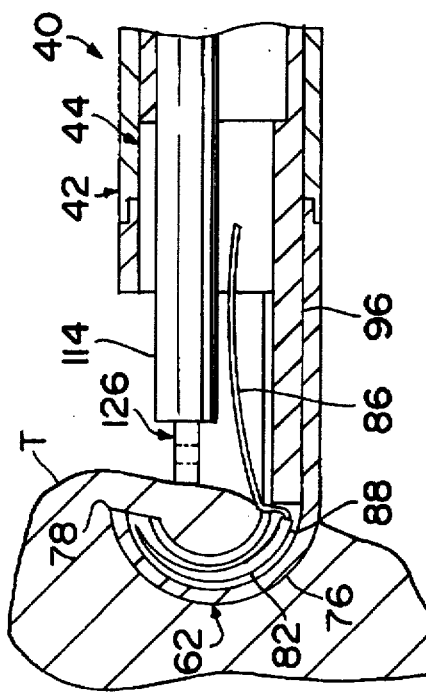
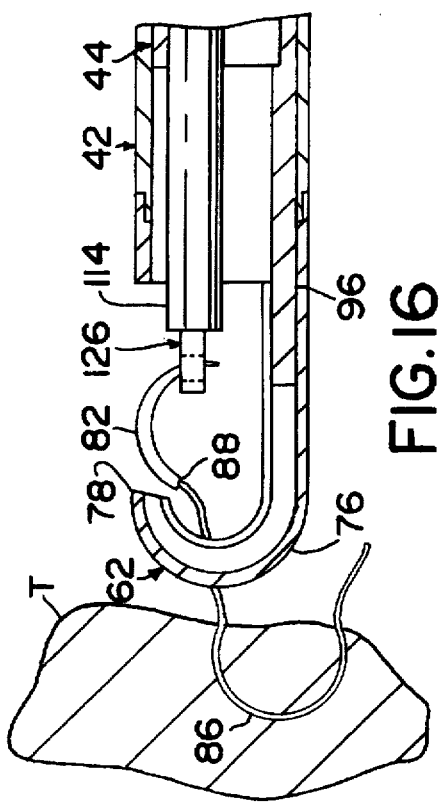
FIG.15
FIG.16
FIG.14

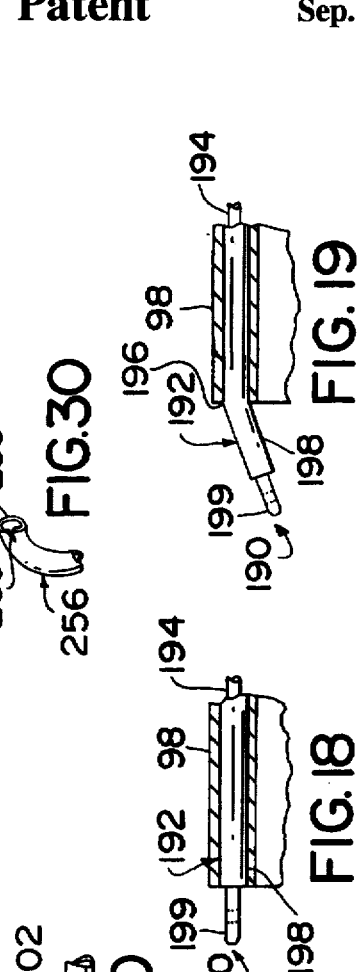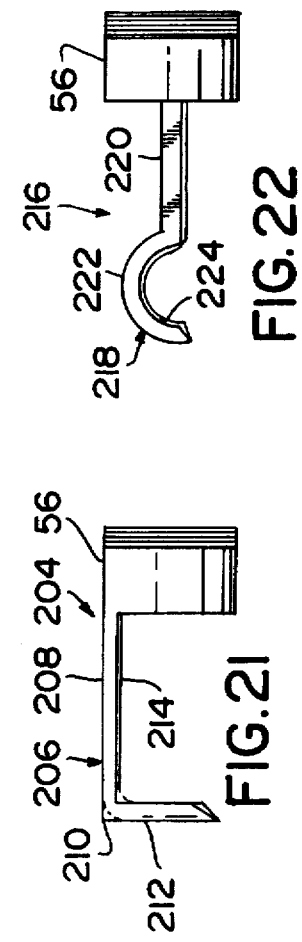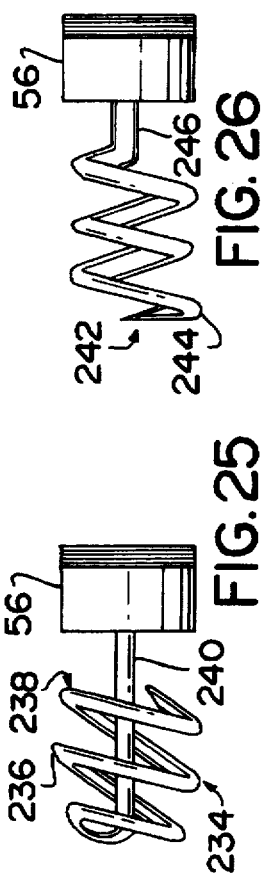

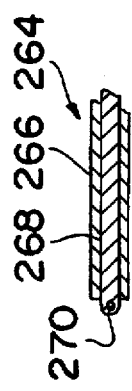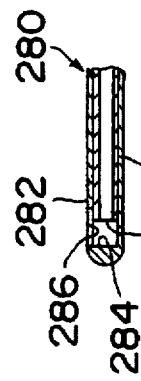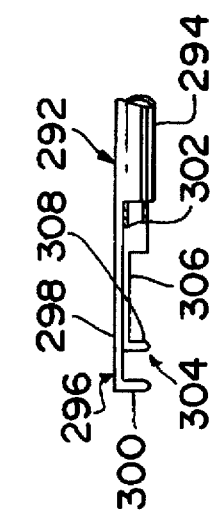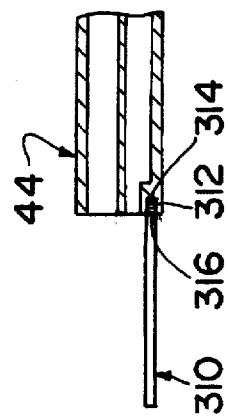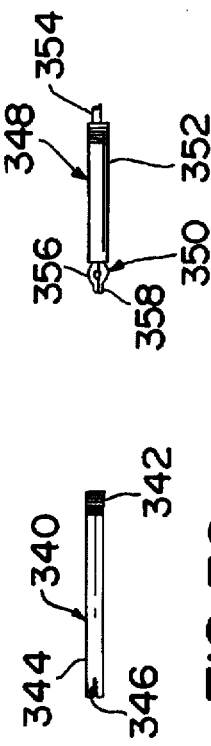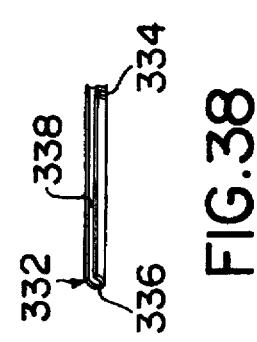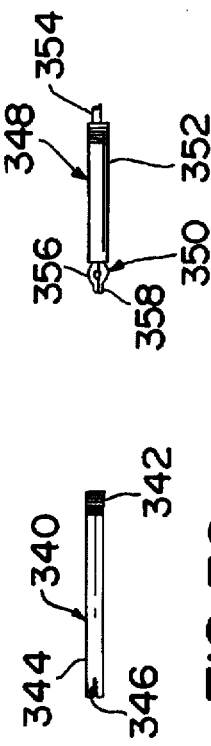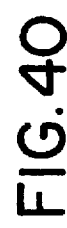

NEEDLE DRIVING APPARATUS AND METHODS OF SUTURING TISSUE

BACKGROUND OF THE INVENTION

1. Field of the Invention

The present invention pertains to suturing of bodily or anatomical tissue and, more particularly, to methods and apparatus for suturing tissue during endoscopic and open surgical procedures.

2. Discussion of the Prior Art

Suturing of bodily tissue is a time consuming part of most surgical procedures including both open surgery and endoscopic or minimally invasive surgery. By "open" surgery is meant surgery wherein the surgeon gains access to the surgical site via a relatively large incision, and by "endoscopic" surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example. In the past, suturing was accomplished with the use of a sharp metal suture needle attached to the end of a length of suture material. Depending on the size of the suture needle and the type of surgery being performed, the suture needle was either grasped manually or with a forceps and caused to penetrate and pass through anatomical tissue thereby pulling the suture material through the tissue. Once the suture material was pulled through the tissue, the surgeon tied a knot in the suture material and adjusted the tension on the suture material to accommodate the particular tissue being sutured and to control approximation, occlusion, attachment or other conditions of the tissue. However, the process of tissue penetration and knotting of the suture material can be time consuming and tedious work, particularly when performed in connection with microsurgery and endoscopic surgery, and can unduly prolong the duration of surgery and therefore the period in which the patient is under anesthesia. Nevertheless, endoscopic surgery is preferred over open surgery due to the greatly reduced trauma and wound healing time for the patient and due to concomitant cost savings associated with shorter hospital stays and performing surgery in non-hospital or out-patient surgery sites. Accordingly, there has been much effort spent to develop techniques for facilitating the suturing normally performed by use of suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery that permit surgeons to suture anatomical tissue using suturing needles and lengths of suture material in a time efficient, consistent and precise manner.

SUMMARY OF THE INVENTION

Accordingly, it is a primary object of the present invention to overcome the above-mentioned disadvantages of the prior art and to improve methods and apparatus for suturing anatomical tissue.

Another object of the present invention is to permit suturing of thick tissue by extending a suture needle from a tissue penetrating tip of a hollow needle guide.

An additional object of the present invention is to expand the range of motions by which a surgeon can drive a needle through anatomical tissue to form a suture.

The present invention has a further object in preventing entanglement of a length of suture material attached to a suture needle when the needle is inserted in an anatomical cavity.

Some of the advantages of the present invention are that suturing of anatomical tissue can be accomplished in a time efficient, consistent and precise manner, that anatomical tissue of varying thickness can be sutured, that suturing can be accomplished using standard suture needles and filamentous suture materials without the need of having to manually grasp the needles thereby reducing the risk of infecting medical personnel, that the size of needles used for suturing thick tissue can be reduced thereby reducing the space needed to suture and facilitating insertion of the needles through portals as part of an endoscopic procedure, and that familiar wrist and arm motions can be utilized alone or in combination with simple hand motions to drive the suture needles through anatomical tissue.

The present invention is generally characterized in an apparatus for suturing anatomical tissue including a hollow needle guide having a distal end, a needle movably disposed within the needle guide and having proximal and distal ends, suture material connected with the needle, and manually articulable needle receiving means coupled with the needle guide for guiding the distal end of the needle as the proximal end of the needle is advanced distally through the needle guide and capturing the needle when the proximal end of the needle emerges from the distal end of the needle guide.

Another aspect of the present invention is generally characterized in an apparatus for suturing anatomical tissue including a hollow needle guide having a sharp tissue penetrating distal end, a needle disposed within the needle guide and having proximal and distal ends, the needle being movable between a retracted position where a distal end of the needle is proximally spaced from the distal end of the needle guide and an extended position where the distal end of the needle protrudes distally from the distal end of the needle guide, and suture material connected with the needle.

A further aspect of the present invention is generally characterized in an apparatus for suturing anatomical tissue including a forceps having opposed jaws defining a hollow needle guide with a distal end, a needle disposed within the needle guide and having proximal and distal ends, the needle being movable between a retracted position where the proximal end of the needle is disposed within the needle guide and an extended position where the proximal end of the needle is disposed externally of the needle guide, and suture material connected with the needle.

Yet another aspect of the present invention is generally characterized in a method of suturing anatomical tissue including the steps of penetrating through the tissue with a distal end of a hollow needle guide and extending a needle carrying suturing material from the distal end of the hollow needle guide.

Still a further aspect of the present invention is generally characterized in a method of suturing anatomical tissue including the steps of positioning a distal end of a hollow needle guide proximate the anatomical tissue to be sutured, extending a needle carrying suture material from the distal end of the hollow needle guide, penetrating through the tissue with the needle, guiding the needle as it is extended from the distal end of the hollow needle guide and capturing the needle when a proximal end of the needle emerges from the distal end of the hollow needle guide.

An additional aspect of the present invention is generally characterized in a method of suturing anatomical tissue including the steps of penetrating part way through the anatomical tissue with a distal end of a hollow needle guide, and extending a needle carrying suture material from the distal end of the hollow needle guide to complete penetration of the anatomical tissue.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 2 is a side view, partly in section, of the suturing apparatus shown in FIG. 1.

FIG. 3 is an exploded fragmentary view of the needle guide and inner member of the suturing apparatus of FIG. 1.

FIG. 4 is an enlarged fragmentary view of the needle receiving assembly of the suturing apparatus of FIG. 1.

FIG. 6 is a side view, partly in section, illustrating a suture needle being loaded into the suturing apparatus of FIG. 1.

FIGS. 7-10 are side views, partly in section, illustrating use of the suturing apparatus of FIG. 1.

FIG. 9A is a side view of a modified needle guide according to the present invention.

FIGS. 14-16 are side views, partly in section, illustrating yet another use of the suturing apparatus of FIG. 1.

FIG. 17 is a fragmentary side view, partly in section, illustrating a modification of the suturing apparatus of the present invention.

FIGS. 18 and 19 are fragmentary side views of a modified needle receiving assembly for the suturing apparatus of the present invention.

FIGS. 20-23, 25 and 26 are side views of alternate needle guide assemblies for use with the suturing apparatus of the present invention.

FIG. 24 is a frontal view of the needle guide assembly shown in FIG. 23.

FIGS. 27-30 are fragmentary side views of alternate distal end configurations for the needle guide assemblies of the present invention.

FIGS. 31-34 are fragmentary side views of alternate needle receiving assemblies for use with the suturing apparatus of the present invention.

FIG. 35 is a fragmentary side view, partly in section, illustrating a modification of an inner member of the suturing apparatus of the present invention.

FIGS. 36-40 are side views illustrating alternate pusher rods for mounting at the distal end of the inner member of FIG. 34.

DESCRIPTION OF THE PREFERRED EMBODIMENTS

Figure 1:
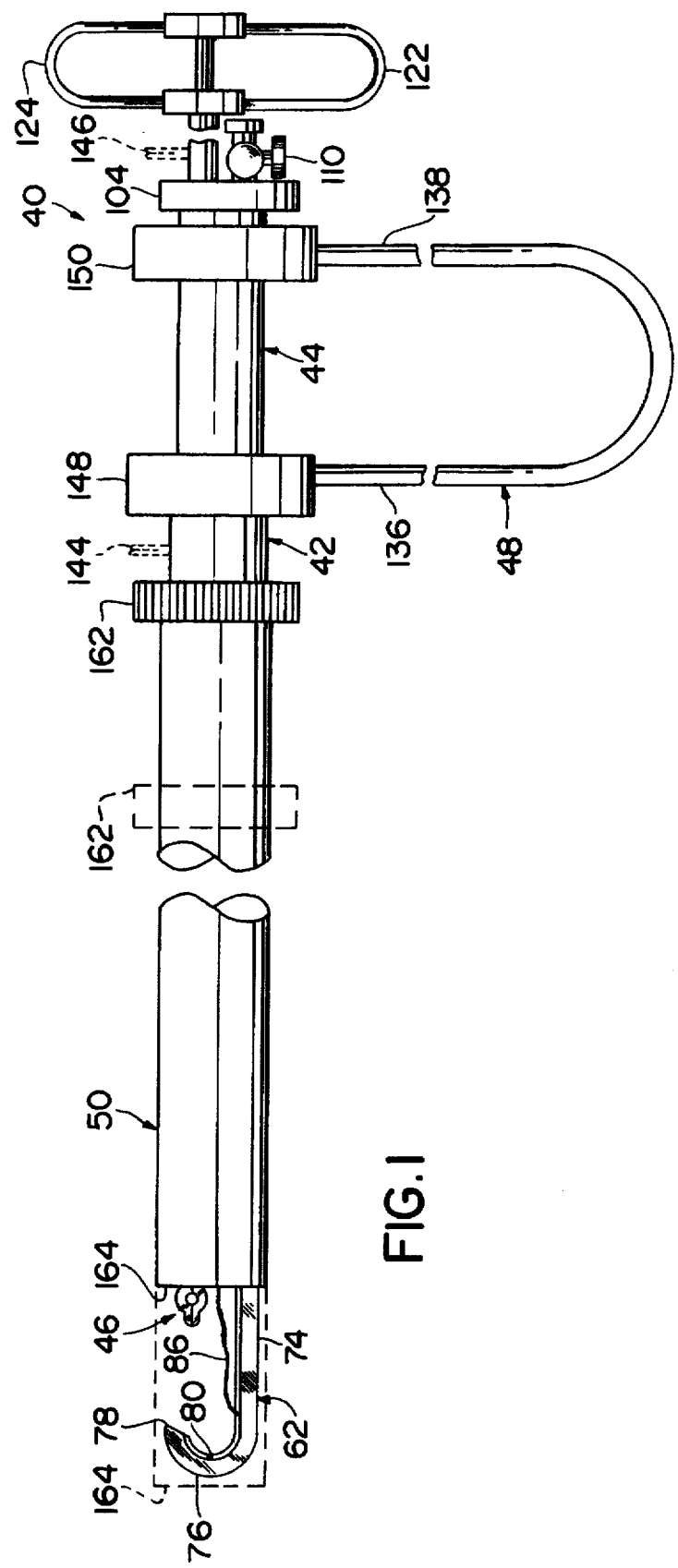
FIG. 1 is a side view of a suturing apparatus according to the present invention.

A suturing apparatus 40 according to the present invention, as shown in FIGS. 1 and 2, includes an outer member 42, an inner member 44 telescopically fitted within the outer member, a needle receiving forceps assembly 46 disposed within the inner member, and a handle assembly 48 connected between proximal ends of the outer member 42 and the inner member 44. Also shown is a protective sleeve 50 telescopically fitted over the outer member 42 for reasons detailed below.

As best seen in FIGS. 2 and 3, outer member 42 includes a tubular body portion 52 and a needle guide assembly 54 at the distal end of the tubular body portion. Tubular body portion 52 and needle guide assembly 54 can be of integral, one-piece construction but are preferably configured in a manner to be detachably coupled. Needle guide assembly 54 includes a cylindrical base 56 having proximal and distal ends 58, 60 and a generally J-shaped needle guide 62 extending from the distal end of the cylindrical base. The proximal end 58 of the cylindrical base 56 is externally threaded as indicated at 68 and the distal end 70 of the tubular body portion 52 includes an internally threaded lumen 72 to matingly receive the needle guide assembly. Needle guide 62 has a proximal shank portion 74 extending from a lateral distal edge of the cylindrical base 56 and a distal curved portion 76 terminating at a sharp, tissue penetrating tip 78. Shank portion 74 and curved portion 76 of the needle guide are hollow and a continuous slot 80 is formed along an inner surface of the needle guide with a size to permit passage of conventional suture material through the slot.

Referring further to FIG. 2, a standard curved suture needle 82 with a tissue penetrating distal end 84 is disposed within the hollow curved portion 76 of the needle guide 62. A length of filamentous suture material 86 extends from a proximal end 88 of the needle and passes through slot 80 into the tubular body portion 52 of the outer member 42. Suture material 86 can be of finite length, in which case the proximal end of the suture material can be disposed within the tubular body portion of the outer member, or the suture material 86 can be fed continuously from a spool mounted at or near a proximal end of the inner member.

Inner member 44 includes an elongate tubular shaft 90 having proximal and distal ends 92, 94 and a solid cylindrical pusher rod 96 extending from a lateral edge of the distal end of the shaft. Pusher rod 96 is preferably made of a flexible or semirigid material that can be sterilized, such as teflon, nylon or a spring steel, and is configured to fit telescopically within needle guide 62 so that when the tubular shaft 90 is fitted within the tubular body portion 52 of the outer member 42 and advanced distally relative to the outer member, the pusher rod 96 will slide through the straight and curved portions 74 and 76 of the needle guide. A cylindrical wall or partition 98 extends longitudinally along an inner surface 100 of inner member 44 diametrically opposed from pusher rod 96 to form a passage 102 for the needle receiving assembly 46. The proximal end 92 of inner member 44 is closed by a cap 104 having an opening therein communicating with passage 102 and another opening 106 communicating with the central lumen 108 defined by the tubular shaft 90. A stopcock valve 110 regulates passage of fluids and instruments through the second opening 106 and thus the central lumen 108. A round flange 112 is distally spaced from the cap 104.

Needle receiving assembly 46 includes a tubular member 114 having proximal and distal ends 116 and 118, a central member 120 telescopically fitted within the tubular member 114, and a pair of U-shaped handles 122 and 124 connecting proximal ends of the central and tubular members. As best shown in FIG. 4, central member 120 has a forceps 126 at a distal end made of a material having sufficient elastic memory to be spring urged into a normally open configuration as shown. The forceps 126 shown include jaws 128 and 130 with opposed grasping surfaces 131 and 133 and opposed concave portions 132 and 134 proximally spaced from the grasping surfaces. Concave portions 132 and 134 cooperate to define a substantially circular aperture when the jaws of the steps are closed together; and, when the forceps is appropriately positioned relative to the needle guide, the aperture serves to guide the distal end of the needle as a proximal end of the needle is advanced distally through the needle guide and also frictionally engages the needle when the proximal end of the needle has emerged from the distal end of the needle guide so that the needle is effectively captured or immobilized. Jaws 128 and 130 can be opened to release the captured suture needle and can also be used to grasp suture material, anatomical tissue and other objects using grasping surfaces 131 and 133. Handles 122 and 124 normally urge proximal ends of the central and tubular members apart so that the distal end of the tubular member will slide over the jaws causing the jaws to close together as shown in FIG. 2.

Referring again to FIG. 2, handle assembly 48 is generally U-shaped and includes a pair of handle members 136 and 138 coupled with the proximal ends of the outer and inner members 42 and 44, respectively. Handle assembly 48 can be bifurcated centrally at 140, as shown in phantom in FIG. 2, and provided with a leaf spring 142 to urge the handle members 136 and 138 apart. Alternatively, the U-shaped handle assembly can be of one-piece spring material construction.

Outer member 42 and/or needle receiving assembly 46 can each carry electrical connectors, as shown in phantom at 144 and 146 in FIGS. 1 and 2, so that the needle guide 62 and/or needle grasping forceps 126 can be utilized as conductive elements in a conventional manner to perform unipolar or bipolar electrosurgical procedures. For example, outer member 42 and needle receiving assembly 46 can both carry an electrical connector and be properly insulated so that the tip of the needle guide 62 and forceps 126 serve as spaced electrodes to form a bipolar electrosurgical instrument.

The suturing apparatus can be provided with parts assembled as shown in FIGS. 1 and 2 or in a disassembled state wherein parts of the suturing apparatus are provided separately and assembled by the user. If provided in a disassembled state, assembly of the parts discussed so far involves choosing an appropriate needle guide assembly based upon the type of anatomical tissue to be sutured and the suture needle to be used and attaching the needle guide assembly to the distal end 70 of the tubular body portion 52 of the outer member 42 as shown in FIG. 3 for needle guide assembly 54. With a needle guide assembly threaded onto the tubular body portion 52 of outer member 42, inner member 44 can be inserted into outer member 42 and rotated to align pusher rod 96 at the distal end of the inner member with the straight shank portion 74 of needle guide 62. Inner member 44 is then advanced distally relative to outer member 42 until pusher rod 96 is received within shank portion 74 of needle guide 62, at which point inner and outer members 44 and 42 are restrained from rotating relative to one another.

Handle assembly 48 can be coupled with outer member 42 and inner member 44 as shown in FIG. 2 by attaching handle member 136 to the proximal end 64 of outer member 42 and handle member 138 to the proximal end 94 of inner member 44. Handle members 136 and 138 include cylindrical collars 148 and 150, respectively, that are slipped over flanges 66 and 112 at the proximal ends of the outer and inner members. As mentioned previously, handle members 136 and 138 are biased apart, for example by a leaf spring 142, so that proximal ends of the outer and inner members 42 and 44 will normally be biased apart as shown in FIG. 2. As a result, pusher rod 96 is normally held in a retracted position near the proximal end of the needle guide 62.

Figure 5:
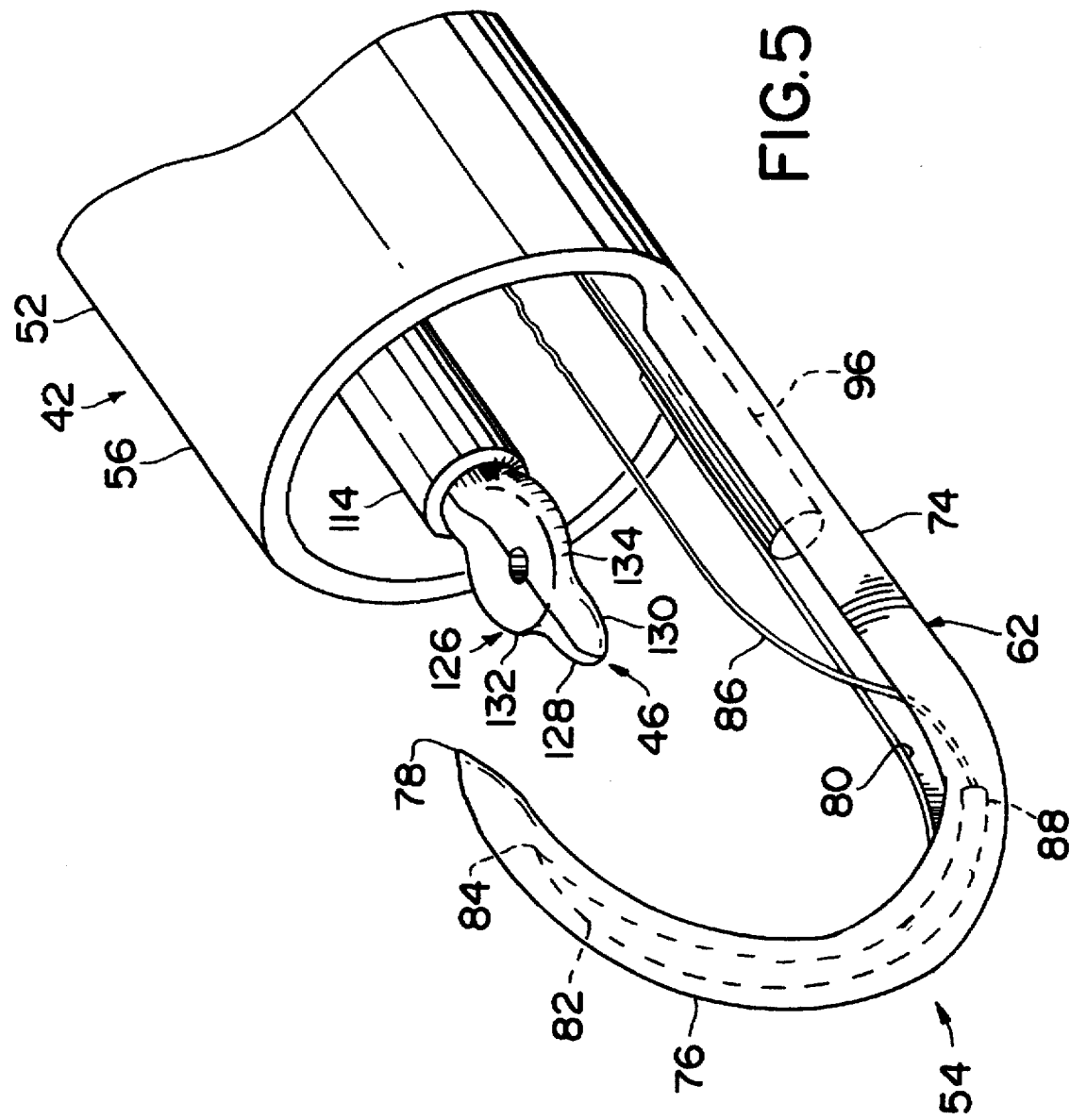
FIG. 5 is a perspective view of the distal end of the suturing apparatus shown in FIG. 1.

If not already installed within inner member 44, needle receiving assembly 46 can be inserted into passage 102 formed by cylindrical wall 98 inside the inner member and advanced distally until forceps 126 is disposed distally of the cylindrical wall. As mentioned previously, forceps 126 is normally closed; and in order to facilitate passage of the forceps through passage 102, concave portions 132 and 134 of the forceps can be configured to extend radially outward no further than tubular member 114. For purposes of clarity, handles 122 and 124 are shown in the plane of the drawing of FIG. 2; however, as can be seen in FIG. 5, in use, forceps 126 is preferably rotated 90° from the position shown in FIG. 2 so that the opening defined between concave portions 132 and 134 of the forceps is aligned with the path of a needle emerging from the distal end of the needle guide.

Suture needle 82 can be loaded into the curved portion 76 of needle guide 62 by inserting the proximal end 88 of the needle into the distal end of the curve needle guide portion and guiding the suture material 86 along slot 80 so that it trails behind the needle. An optional loading device, shown in FIG. 6 at 152, can be used to load the needle into the needle guide 62 without fear of contacting the sharp tip 78 of the needle guide. The loading device 152 resembles a funnel with a hollow conical mouth portion 154 tapering to a curved throat portion 156 configured to fit within or around the needle guide. In use, the throat portion 156 of the loading device is fitted against the open distal end of needle guide 62 and needle 82 is dropped into the mouth portion and received within the needle guide, after which the loading device is removed.

Needle 82 conforms substantially to the curvature at the distal end of needle guide 62 and is thus prevented from migrating into the straight shank portion 74 of the needle guide by geometrical constraint. In the loaded or retracted position, shown in FIG. 2, the sharp, tissue penetrating tip 84 of the needle is proximally spaced from the sharp tip 78 of the needle guide 62 and the proximal end 88 of the needle is distally spaced from the distal end of the pusher rod 96.

Referring still to FIG. 2, it can be seen that, in use, handle assembly 48 can be grasped by the user and manipulated by use of various wrist and arm motions to position the suturing apparatus 40 at a surgical site without inducing substantial relative movement between outer and inner members 42 and 44 of the apparatus. Accordingly, one method of suturing anatomical tissue with the suturing apparatus, as shown in FIGS. 7–10, involves utilizing the needle guide 62 as a needle to penetrate through anatomical tissue T with the suture needle 82 in the retracted position. More specifically, the sharp tip 78 of needle guide 62 is used to penetrate into the anatomical tissue by appropriate manipulation of the suturing apparatus and is passed through the tissue until the tip emerges from the tissue at a location spaced from the point of initial penetration as shown in FIG. 7. Turning again to FIG. 2, it can be seen that needle receiving assembly 46 can be advanced distally relative to inner member 44 and rotated appropriately to position forceps 126 at a location suitable for receiving the curved suture needle 82 when the needle protrudes from needle guide 62.

Referring still to FIG. 2, it will also be seen that needle 82 can be driven through needle guide 62 by squeezing handle members 136 and 138 together which, in turn, causes inner member 44 to be advanced distally relative to outer member 42 and pusher rod 96 to slide within needle guide 62 into abutment with the proximal end 88 of needle 82. Pusher rod 96 is flexible and can thus conform to the shape of needle guide 62 as the rod is advanced. Continued squeezing of handle members 136 and 138 toward one another causes pusher rod 96 to drive needle 82 in a distal direction through needle guide 62, as shown in FIG. 8, until the tip 84 of needle 82 emerges from the distal end of the needle guide and is received by the aperture formed between jaws of the forceps 126. Suture material 86 is pulled through the tissue T along slot 80 in response to distal movement of needle 82. The shape and size of the aperture are such that, when the proximal end 88 of needle 82 emerges from needle guide 62, the needle is captured between jaws of the forceps and frictionally engaged so that handle pressure can be reduced, allowing pusher rod 96 to recede from the curved portion 76 of needle guide 62 to its original position within the straight shank portion 74. Suture material 86 is attached to the proximal end 88 of needle 82 and thus remains threaded through the anatomical tissue T when the needle guide is removed from the tissue as shown in FIG. 9. If necessary, needle receiving assembly 46 can be manually moved proximally relative to inner member 44 to facilitate removal of the needle guide from the tissue by increasing the spacing between the distal end of the needle guide and the forceps.

For purposes of illustration, a spherical knotting element 158 is shown schematically in FIG. 9 attached to the proximal end of the suture material to serve as a knot for joining opposite ends of the suture material into a loop; however, any type of suture material or knotting technique can be used. A forceps 160 is used to grasp the knotting element 158 in such a way that the distal end of the suture material is received within an engaging portion of the knotting element, and the knotting element is moved toward tissue T while the suturing apparatus 40 is retracted to adjust the tension of the suture material. Alternatively, the needle guide 62 could be formed of laterally opposed jaws 161, 163 of a forceps 165, as shown in FIG. 9A, such that grasping and manipulation of the knotting element can be performed without the need for a separate forceps. The modified needle guide is preferably coupled with any suitable handle structure, such as handle assembly 48, such that the jaws can be normally biased to a closed condition to form a tissue penetrating tip 167 and opened manually when it is desired to grasp an object such as knotting element 158. When the suture material is appropriately tensioned, the knotting element can be closed around the suture material to form a closed loop suturing the tissue as shown in FIG. 10. Various types of knotting elements that can be used with the suturing apparatus of the present invention are described in copending patent applications Ser. No. 08/366,285, filed Dec. 29, 1994 and Ser. No. 08/377,723, filed Jan. 25, 1995, the disclosures of which are incorporated herein by reference.

Figure 13:
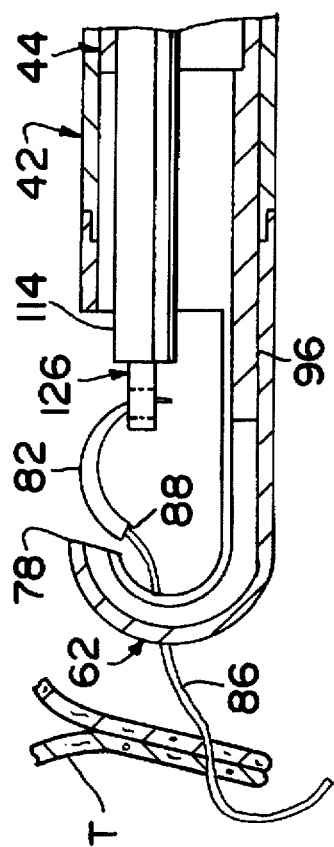
FIGS. 11-13 are side views, partly in section, illustrating another use of the suturing apparatus of FIG. 1.
Figure 11:
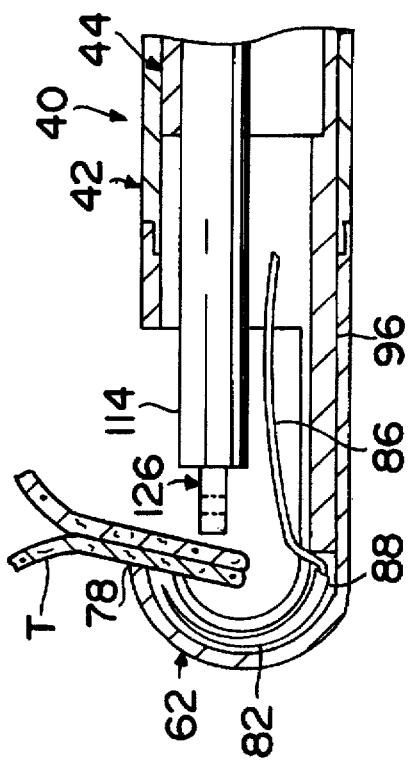
Figure 12:
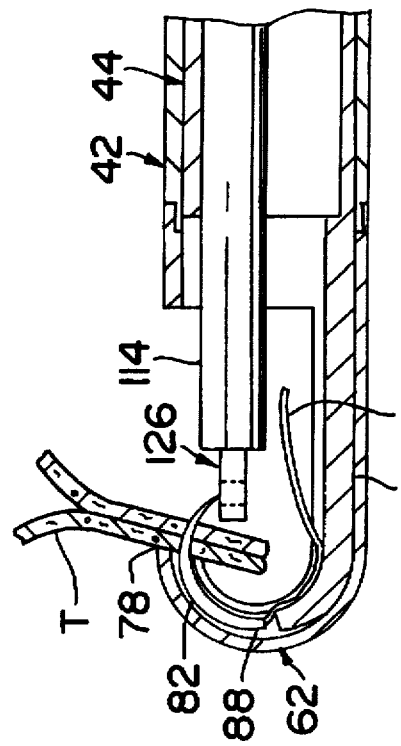

Another method of suturing anatomical tissue according to the present invention is illustrated in FIGS. 11–13 wherein only the suture needle is utilized in penetrating the tissue. The suturing apparatus 40 is manipulated to position anatomical tissue T between the distal tip 78 of needle guide 62 and forceps 126. Needle guide tip 78 is then positioned proximate the tissue, as shown in FIG. 11, to precisely locate the point of entry for suture needle 82. Pusher rod 96 is advanced in the manner previously described, driving needle 82 and suture material 86 through needle guide 62 and into the tissue as illustrated in FIG. 12. When the distal end of the needle penetrates through the tissue, the needle is received by forceps 126 and held therein during the tying procedure as shown in FIG. 13.

FIGS. 14–16 illustrate yet another method of suturing anatomical tissue according to the present invention wherein the needle guide 62 is utilized as a needle to penetrate anatomical tissue part way through the thickness of the tissue and suture needle 82 is extended to complete penetration through the tissue. It will be appreciated, therefore, that use of the suturing apparatus 40 in such a manner permits suturing of anatomical tissue thicker than that normally able to be sutured by use of the suture needle alone. The method involves penetrating into anatomical tissue T using the tip 78 of needle guide 62 and positioning the curved portion 76 of the needle guide within the tissue as shown in FIG. 14 such that a portion of the anatomical tissue is positioned between tip 78 of needle guide 62 and forceps 126. Pusher rod 96 is then advanced distally by squeezing handle members 136 and 138 together to extend suture needle 82 from the tip of the needle guide and through the tissue positioned between the tip and forceps as illustrated in FIG. 15. Needle 82 is received by forceps 126 and held therein while needle guide 62 is removed from the tissue leaving suture material 86 in place within the tissue to form a suture using any conventional knotting or tying technique.

The suturing apparatus can be used to suture anatomical tissue in open or endoscopic procedures. In the case of endoscopic procedures, the suturing apparatus will be inserted into an anatomical cavity through a portal formed in the wall of the cavity; and, it will be appreciated that the sharp needle guide of the suturing apparatus can snag structures within the portal or the anatomical cavity. Referring to FIG. 1, it will be seen that protective sleeve 50 can be used to cover the needle guide 62 of the suturing apparatus 40 when the apparatus is inserted through a portal or any time it is desired that the needle guide not be exposed. Protective sleeve 50 is telescopically fitted over outer member 42 and includes a collar 162 at a proximal end for being grasped by the user. Collar 162 can be grasped and moved distally, as shown by phantom line in FIG. 1, to position the distal end 164 of protective sleeve 50 around needle guide 62 so as to protect the needle guide during insertion. Once positioned within the anatomical cavity, sleeve 50 can be retracted or moved proximally to expose the needle guide prior to suturing tissue.

FIG. 17 illustrates a modification of the suturing apparatus according to the present invention wherein the modified suturing apparatus 166 includes an inner member 168 similar to inner member 44 but with a cylindrical housing 170 at a proximal end and a needle receiving assembly 172 coupled with the housing. Tubular member 174 of the needle receiving assembly is similar to tubular member 114 and, in addition, includes a flange 176 near a proximal end of the tubular member. Flange 176 is disposed within housing 170 and is biased toward a proximal end wall 178 of the housing by a helical coil spring 180 disposed around tubular member 174 and held in compression between a distal end wall 182 of housing 170 and flange 176. Suturing apparatus 166 also differs in that the central member 184 of the needle receiving assembly is hollow and a valve 186 is mounted at a proximal end of the central member to control passage of fluids and instruments through the central member.

Referring still to FIG. 17, it can be seen that, in use, inner member 168 can be moved distally relative to an outer member by operation of handle assembly 188. As described previously in connection with suturing apparatus 40, distal movement of the inner member will cause a pusher rod at the end of the inner member to slide through a needle guide into abutting relation with a suture needle disposed within the needle guide. Housing 170 is also moved distally relative to the outer member causing proximal end wall 178 of the housing to bear against flange 176 of tubular member 114 driving the needle receiving assembly 172 forward in a distal direction at the same time the needle is driven from the needle guide by the pusher rod. As a result, the suture needle can be extended and received by the needle receiving assembly in response to a single hand motion such that the number of hand motions required to suture are reduced and the suturing procedure is simplified.

FIGS. 18 and 19 illustrate a modified needle receiving assembly 190 for use with the suturing apparatus of the present invention wherein the distal end 192 of the modified needle receiving assembly has a predetermined shape and is made of a material having an elastic memory such that the needle receiving assembly normally assume, the predetermined shape when in a relaxed state. For example, central member 194 of needle receiving assembly 190 can have a predetermined shape with a bend 196 and tubular member 198 can be made of a flexible material to conform to the shape of the central member. In the position shown in FIG. 18, needle receiving assembly 190 is prevented from bending because the normally bent portion of the assembly is telescopically fitted within a relatively rigid straight section of the cylindrical wall 98. When needle receiving assembly 190 is advanced distally relative to the cylindrical wall 98, as shown in FIG. 19, the assembly assumes the predetermined shape, which can for example be chosen to facilitate positioning of the forceps 199 to receive a particular type of suture needle. Needle receiving assembly 190 can have any predetermined shape useful for suturing tissue, including bent or curved configurations, for example.

Referring now to FIGS. 20–25, various needle guide assemblies for mounting on the distal end of the outer member 42 are shown. In accordance with the present invention, these modified needle guide assemblies share a common base structure 56 so that they can be readily interchanged depending on the specific surgical application for the suturing apparatus of the present invention. The needle guide assembly illustrated in FIG. 20 at 200 is similar to needle guide assembly 54 but with a hollow needle guide 202 having a continuous outer surface without a slot. FIG. 21 shows a needle guide assembly 204 having a generally L-shaped needle guide 206 with a straight proximal portion 208 extending from a distal edge of the base 56 to a bend 210 joining the shank with a straight distal portion 212 oriented substantially perpendicular to a longitudinal axis of the needle guide. Proximal and distal portions 208 and 212 of the needle guide are hollow and are shown with a slot 214 extending continuously along an inside surface of the needle guide. Bend 210 of the needle guide is shown as being acutely angled but can also be curved as shown in phantom in FIG. 21. Another needle guide assembly is illustrated in FIG. 22 wherein the needle guide assembly 216 includes a needle guide 218 having a straight proximal portion 220 extending from base 56 along a central longitudinal axis of the base, for example from a support extending diametrically across the open distal end of the base, and an arcuate distal portion 222 extending distally from the straight proximal portion of the needle guide in a plane containing the central longitudinal axis of the needle guide. A slot 224 extends continuously along the length of the needle guide 218. Needle guide assembly 226, as shown in FIGS. 23 and 24, includes a needle guide 228 having a straight proximal portion 230 similar to that shown in FIG. 22 and an arcuate distal portion 232 forming multiple coils of increasing diameter in a plane perpendicular to the longitudinal axis of the needle guide. The needle guide assembly 234 shown in FIG. 25 is similar to needle guide assembly 226 but with an arcuate portion 236 of the needle guide 238 coiling around the straight proximal portion 240 in a proximal direction. FIG. 26 shows another modification of the needle guide assembly wherein the modified needle guide assembly 242 is similar to needle guide assembly 226 but with the arcuate portion 244 forming coils that protrude distally from the straight portion 246 like a corkscrew.

The needle guides shown and described herein can have various distal end configurations, as illustrated in FIGS. 27–31, depending on the operational requirements of the suturing apparatus and the tissue to be sutured. For example, a needle guide distal end 248 having a sharp tissue penetrating tip 250 and a small notch 252 formed near the tip is shown with a slot 254 in FIG. 27 and without a slot in FIG. 28. Another needle guide distal end 256 including a blunt tissue penetrating tip 258 and a notch 260 formed near the tip is shown with a slot 262 in FIG. 29 and without a slot in FIG. 30. Notches 252 and 260 are generally V-shaped to receive and frictionally engage suture material drawn into the notches so that the suture material can be held in a fixed position relative to the needle guide during knotting and tying procedures.

Various needle receiving assemblies that can be used with the suturing apparatus of the present invention to guide and capture suture needles extended from a needle guide are shown in FIG. 31–33. The needle receiving assembly 264 shown in FIG. 31 includes a tubular member 266 like tubular member 114 and a central member 268 with an eyelet 270 at a distal end. Eyelet 270 can be protruded distally from tubular member 266 by operation of a handle mechanism (such as handles 122 and 124) to receive a suture needle, but is biased to a retracted position so that when the handles are released, the needle is captured between the eyelet and a distal end of the tubular member. FIG. 32 illustrates yet another needle receiving assembly 272 having a tubular member 274 and a central member 276 with a hollow cylindrical segment 278 mounted transversely at the distal end of the central member for receiving and frictionally engaging a suture needle. Yet another needle receiving assembly is shown in FIG. 33 at 280 wherein the tubular member 282 of the needle receiving assembly is closed at a distal end to form a forceps jaw 284 and an aperture 286 is formed in a sidewall of the tubular member at a position proximally spaced from forceps jaw 284 to permit passage of a suture needle into the tubular member. Central member 288 of needle receiving assembly 280 is movable within the tubular member and is biased in a distal direction so that the distal end 290 of the central member functions as an opposed forceps jaw to capture the suture needle passing through aperture 286. The needle receiving assembly 292 shown in FIG. 34 is similar to needle receiving assembly 280; however, the tubular member 294 carries an L-shaped outer jaw 296 having longitudinal and transverse legs 298 and 300 and the central member 302 carries an L-shaped inner jaw 304 having a longitudinal leg 306 that slides within the longitudinal leg of the outer jaw and a transverse leg 308 that can be moved toward the transverse leg of the outer jaw to perform the functions of a forceps such as, for example, capturing suture needles, holding suture material or applying knotting elements.

Referring now to FIGS. 35–40, various pusher rods for mounting on the distal end of the inner member 44 are shown. In accordance with the present invention, these modified pusher rods can be formed as an integral part of the inner member or can be configured to be detachably coupled with the inner member so as to be readily interchanged depending on the operational requirements of the suturing apparatus of the present invention. The pusher rod illustrated in FIG. 35 at 310 is similar to pusher rod 96 but with threads 312 at a proximal end 314 for being received by a threaded receptacle 316 formed at the distal end of the inner member. FIG. 36 shows a pusher rod 318 which is similar to pusher rod 310 but with a rounded distal end 320. Another modified pusher rod, shown in FIG. 37 at 322, includes a hollow tube 324 with a flat or rounded distal end 326 and a threaded proximal end 328 for being received by a threaded bore 330 formed at the distal end of the inner member in communication with the central lumen. The hollow pusher rod 322 can thus be used to pass fluids and/or suture material through the needle guide. FIG. 38 illustrates another hollow pusher rod 332 having a threaded proximal end 334, a rounded or flat distal end 336 and a slot 338 formed longitudinally between proximal and distal ends of the pusher rod, for example to permit lateral passage of suture material into and out of the pusher rod. The modified pusher rod shown in FIG. 39 at 340 can be hollow or solid and includes a proximal end 342, a distal end 344 and a notch 346 formed at the distal end for holding suture material. Yet another modified pusher rod 348 includes a forceps 350 for grasping the proximal end of a suture needle so that the needle can be retracted proximally into the needle guide from an extended position, for example after the suture material has been grasped. Forceps 350 includes a tube 352 and an elongate member 354 disposed within the tube. The elongate member 354 has a pair of opposed jaws 356 and 358 at a distal end that are elastically biased apart. A handle assembly (not shown) can be connected between the tube 352 and the elongate member 354 to normally bias the tube over the jaws 356 and 358 so that the jaws are closed to form a needle driving distal end and can be opened to receive the proximal end of the suture needle.

From the above, it will be appreciated that the suturing apparatus of the present invention can be used to suture anatomical tissue of varying thickness by positioning a hollow needle guide adjacent to, within or through the tissue to be sutured and extending a suture needle carrying suture material from the distal end of the needle guide. Any type of suture needle can be utilized with the suturing apparatus including, for example, straight or curved and blunt or sharp needles in hollow or solid configurations with or without slots. The suture material can be attached to the suture needle at proximal, distal or intermediate portions of the needle or advanced through the suture needle if the needle is hollow. Also, the suture needles can have two or more lengths of suture material attached. In addition, the suturing apparatus can be used to apply bioabsorbable suture needle devices such as those described in U.S. Pat. Nos. 4,932,962, 4,981,149 and 5,074,874 to Yoon et al; and 5,053,047, 5,222,976 and 5,330,503 to Yoon; the disclosures of which are incorporated herein by reference. The needle guide can have any configuration for carrying a suture needle, including straight or curved configurations with blunt or sharp tissue penetrating tips. By "hollow" is meant defining a passage or lumen between open ends; and, in addition to being hollow, the needle guides of the present invention can also have slots formed part way or along the entire length of the needle guides in communication with the lumens to permit passage of suture material from spaces within the suturing apparatus to points of attachment with suturing needles disposed within the needle guides. Needle receiving assemblies mounted by the suturing apparatus can be moved axially, bent transversely and, in the case of forceps, opened or closed to grasp the suture needle, suture material or a knotting element, such as the knotting element shown schematically in FIGS. 7–10 and described in my pending patent application Ser. Nos. 08/366,285 and 08/377,723, filed Dec. 29, 1994 and Jan. 25, 1995, respectively. Moreover, axial movement of the needle receiving assemblies can be indexed for a particular suture needle curvature.

While electrical connectors have been shown and described as forming contacts with the outer member and/or needle receiving assembly of the suturing apparatus, it will be appreciated that any number of conventional electrical connectors can be positioned at various locations and connected with various components of the suturing apparatus for performing unipolar or bipolar electrosurgical procedures. Also, inner surfaces of the outer member, inner member or any other member defining a passage or lumen through the suturing apparatus can be electrically insulated to permit insertion of electrosurgical instruments through the passage as a backup.

The U-shaped handles shown and described herein for sliding the inner member within the outer member are exemplary of the types of conventional handle mechanisms suitable for use with the suturing apparatus of the present invention; and, accordingly, the handles can have any configuration for producing relative movement between components of the suturing apparatus including, for example, scissors-type handles having crossed legs with a pivot, handles having a fixed leg or grip connected with one component and a pivoted leg connected with the other component, and pistol grips having movable triggers. Moreover, the handles can have any orientation relative to the longitudinal axis of the suturing apparatus including, for example, substantially transverse orientations whereby the handles extend transversely from a longitudinal axis of the suturing apparatus, substantially longitudinal orientations whereby the handles extend longitudinally from a proximal end of the apparatus or rotatable configurations whereby the handles can be moved between transverse and longitudinal orientations as desired.

The components of the suturing apparatus of the present invention can be made of any suitable, medical grade materials to permit sterilization for re-use or for single patient use. The components can be made of multiple parts of various configurations and materials to reduce cost. The various passages and lumens formed through the apparatus can have various valves, stop cocks and seals to control the flow of fluid and instruments therethrough, such as the valve 110 shown in FIG. 1 or the valve shown in FIG. 17 at 186.

It will also be appreciated that the suturing apparatus of the present invention can be used to apply single or multiple stitches in open or endoscopic surgical procedures. Furthermore, the central channel of the suturing apparatus can be used for irrigation or aspiration and can serve as a space for holding the suture material or as a portal for the introduction of medical instruments. The features of the various embodiments described above can be combined in any manner desired dependent upon the operational requirements of the procedure to be performed and the complexity of the suturing apparatus.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An apparatus for suturing anatomical tissue comprising a hollow needle guide having a distal end; a needle movably disposed within said needle guide and having proximal and distal ends; suture material connected with said needle; and manually articulable needle receiving means coupled with said needle guide for guiding said distal end of said needle as said proximal end of said needle is advanced distally through said needle guide and capturing said needle when said proximal end of said needle emerges from said distal end of said needle guide.

2. An apparatus as recited in claim 1 wherein said needle receiving means includes a forceps having a pair of jaws with concave portions in opposed relation for receiving said needle when said jaws are closed together.

3. An apparatus as recited in claim 2 wherein said jaws are biased apart and said forceps further includes a tubular member disposed around said jaws and movable between a retracted position allowing said jaws to open and an extended position drawing said jaws together.

4. An apparatus as recited in claim 3 wherein said jaws include opposed grasping surfaces axially spaced from said concave portions.

5. An apparatus as recited in claim 4 and further comprising a handle coupled with said jaws and said tubular member for creating relative movement between said jaws and said tubular member.

6. An apparatus as recited in claim 1 wherein said needle receiving means includes a rod disposed within a tube and having an eyelet formed at a distal end for receiving said needle when said needle is in said extended position.

7. An apparatus as recited in claim 6 and further comprising a handle coupled with said rod and said tubular member for creating relative movement between said rod and said tubular member.

8. An apparatus as recited in claim 1 wherein said needle receiving means includes a tube having a closed distal end with a side opening and a central member disposed within the tube.

9. An apparatus as recited in claim 8 and further comprising a handle coupled with said tube and said central member for creating relative movement between said tube and said central member.

10. An apparatus as recited in claim 1 wherein said needle receiving means includes a rod with a hollow cylinder mounted transversely at a distal end.

11. An apparatus as recited in claim 1 wherein said needle receiving means is manually movable in an axial direction relative to said needle guide.

12. An apparatus as recited in claim 11 wherein said needle receiving means has a predetermined shape to assume an appropriate position for receiving said needle when moved axially in a distal direction.

13. An apparatus as recited in claim 1 and further comprising needle driving means disposed proximally of said needle for pushing said needle distally through said needle guide from said retracted position to said extended position.

14. An apparatus as recited in claim 13 wherein said needle driving means includes a pusher rod configured to fit within said needle guide.

15. An apparatus as recited in claim 14 wherein said pusher rod is a solid cylinder.

16. An apparatus as recited in claim 14 wherein said pusher rod is a hollow cylinder.

17. An apparatus as recited in claim 15 wherein said pusher rod is slotted.

18. An apparatus as recited in claim 14 wherein a distal end of said pusher rod is notched.

19. An apparatus as recited in claim 14 wherein said pusher rod includes a forceps.

20. An apparatus as recited in claim 14 and further comprising an outer member mounting said needle guide at a distal end and an inner member disposed within said outer member and mounting said pusher rod.

21. An apparatus as recited in claim 20 wherein said inner member defines a central lumen.

22. An apparatus as recited in claim 21 and further comprising a handle coupled with said inner and outer members for creating relative movement between said inner and outer members.

23. An apparatus as recited in claim 1 wherein said needle guide is slotted.

24. An apparatus as recited in claim 1 wherein said distal end of said needle guide includes a notch for holding said suture material.

25. An apparatus for suturing anatomical tissue comprising
   a hollow needle guide having a sharp tissue penetrating distal end;
   a needle disposed within said needle guide and having proximal and distal ends, said needle being movable between a retracted position where a distal end of said needle is proximally spaced from said distal end of said needle guide and an extended position where said distal end of said needle protrudes distally from said distal end of said needle guide; and
   suture material connected with said needle.

26. An apparatus for suturing anatomical tissue, comprising;
   a hollow needle guide having a sharp tissue penetrating distal end;
   a needle disposed within said needle guide and having proximal and distal ends, said needle being movable between a retracted position where a distal end of said needle is proximally spaced from said distal end of said needle guide and an extended position where said distal end of said needle protrudes distally from said distal end of said needle guide;
   suture material connected with said needle;
   wherein said needle guide is slotted.

27. An apparatus for suturing anatomical tissue, comprising:
   a hollow needle guide having a sharp tissue penetrating distal end;
   a needle disposed within said needle guide and having proximal and distal ends, said needle being movable between a retracted position where a distal end of said needle is proximally spaced from said distal end of said needle guide and an extended position where said distal end of said needle protrudes distally from said distal end of said needle guide;
   suture material connected with said needle;
   wherein said distal end of said needle guide is notched to hold said suture material.

28. An apparatus for suturing anatomical tissue, comprising;
   a hollow needle guide having a sharp tissue penetrating distal end;
   a needle disposed within said needle guide and having proximal and distal ends, said needle being movable between a retracted position where a distal end of said needle is proximally spaced from said distal end of said needle guide and an extended position where said distal end of said needle protrudes distally from said distal end of said needle guide;

suture material connected with said needle; and an outer member having proximal and distal ends, wherein said needle guide is mounted on said distal end of said outer member.

29. An apparatus as recited in claim 28 and further comprising an inner member telescopically fitted within said outer member and having a pusher rod at a distal end for being advanced through said needle guide.

30. An apparatus as recited in claim 29 wherein said inner member defines a central lumen.

31. An apparatus as recited in claim 30 and further comprising a handle coupled with said inner and outer members for creating relative movement between said inner and outer members.

32. An apparatus for suturing anatomical tissue comprising a forceps having opposed jaws defining a hollow needle guide with a distal end;

a needle disposed within said needle guide and having proximal and distal ends, said needle being movable between a retracted position where said proximal end of said needle is disposed within said needle guide and an extended position where said proximal end of said needle is disposed externally of said needle guide; and suture material connected with said needle.

33. An apparatus as recited in claim 32 wherein said distal end of said hollow needle guide forms a sharp tissue penetrating tip.

34. A method of suturing anatomical tissue comprising the steps of penetrating through the anatomical tissue with a distal end of a hollow needle guide; and extending a needle carrying suture material from the distal end of the hollow needle guide.

35. A method of suturing anatomical tissue as recited in claim 34 wherein said extending step includes guiding a distal end of the needle as a proximal end of the needle is advanced distally through the hollow needle guide.

36. A method of suturing anatomical tissue as recited in claim 35 and further comprising the step of capturing the needle when the proximal end of the needle emerges from the distal end of the hollow needle guide.

37. A method of suturing anatomical tissue comprising the steps of positioning a distal end of a hollow needle guide proximate the anatomical tissue to be sutured;

extending a needle carrying suture material from the distal end of the hollow needle guide;

penetrating through the anatomical tissue with the needle;

guiding a distal end of the needle as a proximal end of the needle is advanced distally through the hollow needle guide; and capturing the needle when the proximal end of the needle emerges from the distal end of the hollow needle guide.

38. A method of suturing anatomical tissue comprising the steps of penetrating partway through the anatomical tissue with a distal end of a hollow needle guide; and extending a needle carrying suture material from the distal end of the hollow needle guide to complete penetration of the anatomical tissue.

39. A method of suturing anatomical tissue as recited in claim 38 wherein said extending step includes guiding a distal end of the needle as a proximal end of the needle is advanced distally through the hollow needle guide.

40. A method of suturing anatomical tissue as recited in claim 39 and further comprising the step of capturing the needle when the proximal end of the needle emerges from the distal end of the hollow needle guide.

* * * * *